United States Patent [19]

Kanaoka et al.

[11] Patent Number: 4,929,547

[45] Date of Patent: May 29, 1990

[54] ANTITUMOR PROTEIN GENE OF STREPTOCOCCUS PYOGENES SU, PLASMIDS CONTAINING THE GENE, TRANSFORMANT CELLS HARBORING THE PLASMIDS, AND PROCESS FOR PRODUCING THE ANTITUMOR PROTEIN

[75] Inventors: Masaharu Kanaoka, Toyonaka; Chigusa Kawanaka, Kobe; Takaharu Negoro, Takarazuka; Hideo Agui, Ikeda, all of Japan

[73] Assignee: Ohgen Research Laboratories, Limited, Ishikawa, Japan

[21] Appl. No.: 946,025

[22] Filed: Dec. 24, 1986

[30] Foreign Application Priority Data

Dec. 28, 1985 [JP] Japan ............................ 60-298014
Aug. 21, 1986 [JP] Japan ............................ 61-194077

[51] Int. Cl.$^5$ ............................ C12P 1/00; C12N 5/00; C12N 1/22; C12N 1/20
[52] U.S. Cl. ............................ 435/69.1; 435/172.3; 435/253.4; 435/320; 435/252.3; 935/21; 935/55; 935/41; 935/72; 530/350; 530/820; 536/27
[58] Field of Search ............................ 435/68, 172.3, 317, 435/885, 320, 253

[56] References Cited

PUBLICATIONS

Yoshida et al, "Jpn. J. Cancer Res. (Gann)", 76, pp. 213–223, Mar. 1985.
Masui et al, "Biotechnology", pp. 81–85, Jan. 1984.
De Boer et al, "Proc. Natl. Acad. Sci. U.S.A.", vol. 80, pp. 21–25, Jan. 1983.

*Primary Examiner*—Thomas G. Wiseman
*Assistant Examiner*—Patricia A. Carson
*Attorney, Agent, or Firm*—Birch, Stewart, Kolasch & Birch

[57] ABSTRACT

Amino acid sequence of N-terminal region of streptococcal acid glycoprotein (SAGP), and antitumor glycoprotein produced by *Streptococcus pyogenes* Su, was determined, and DNA probes which are complementary to SAGP gene were synthesized.

Chromosomal DNA fragment of *S.pyogenes* Su, which hybridized with those probes was cloned into *E.coli*, and a restriction map of plasmid DNA harboring SAGP gene was revealed and upon it, DNA sequence or amino acid sequence of SAGP gene was determined.

12 Claims, 5 Drawing Sheets

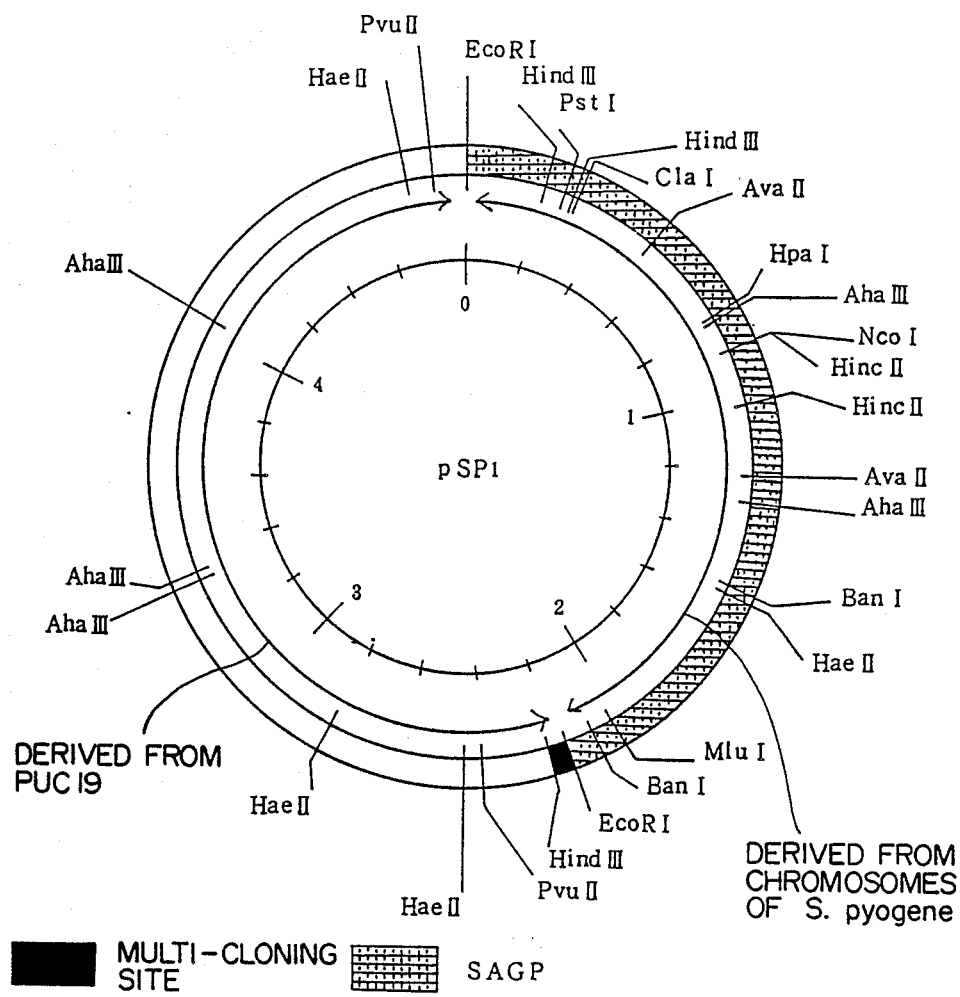
Fig. 1 RESTRICTION ENZYME MAP OF pSP1

Fig. 2-1

```
         10        20        30        40        50        60
GAATTCACAAAAACCAATTAGAAAGAGGTAATTCTTATGACTGCTCAAACACCAATTCAT
                                    MetThrAlaGlnThrProIleHis 70        80        90       100       110       120
GTTTATTCTGAAATTGGAAAATTAAAAAAAGTGTTGCTCCACAGACCCGGTAAAGAAATT
ValTyrSerGluIleGlyLysLeuLysLysValLeuLeuHisArgProGlyLysGluIle 130       140       150       160       170       180
GAAAATCTTATGCCAGACTACTTGGAACGCTTGTTGTTTGATGACATTCCATTCTTAGAG
GluAsnLeuMetProAspTyrLeuGluArgLeuLeuPheAspAspIleProPheLeuGlu 190       200       210       220       230       240
GATGCCCAAAAAGAACATGATGCTTTTGCCCAAGCTTTGCGTGACGAAGGTATTGAAGTC
AspAlaGlnLysGluHisAspAlaPheAlaGlnAlaLeuArgAspGluGlyIleGluVal 250       260       270       280       290       300
TTGTACCTTGAGACCTTAGCTGCAGAATCTCTTGTCACTCCAGAAATTCGCGAAGCTTTC
LeuTyrLeuGluThrLeuAlaAlaGluSerLeuValThrProGluIleArgGluAlaPhe 310       320       330       340       350       360
ATCGATGAATACCTAAGTGAAGCTAATATCCGTGGAAGAGCTACTAAAAAAGCCATTCGT
IleAspGluTyrLeuSerGluAlaAsnIleArgGlyArgAlaThrLysLysAlaIleArg 370       380       390       400       410       420
GAATTGTTGATGGCTATCGAAGACAATCAAGAATTGATTGAAAAAACCATGGCAGGAGTT
GluLeuLeuMetAlaIleGluAspAsnGlnGluLeuIleGluLysThrMetAlaGlyVal 430       440       450       460       470       480
CAAAAATCTGAACTTCCAGAGATCCCAGCATCTGAAAAAGGCTTGACTGACTTGGTTGAA
GlnLysSerGluLeuProGluIleProAlaSerGluLysGlyLeuThrAspLeuValGlu 490       500       510       520       530       540
TCCAATTACCCATTTGCCATCGACCCAATGCCAAACCTTTATTTCACACGGGACCCATTC
SerAsnTyrProPheAlaIleAspProMetProAsnLeuTyrPheThrArgAspProPhe 550       560       570       580       590       600
GCAACTATCGGTACAGGTGTTTCTCTTAACCACATGTTCTCAGAAACACGTAACCGTGAA
AlaThrIleGlyThrGlyValSerLeuAsnHisMetPheSerGluThrArgAsnArgGlu 610       620       630       640       650       660
ACCCTTTATGGTAAATACATTTTCACTCATCACCCAATTTATGGGGGTGGCAAAGTGCCT
ThrLeuTyrGlyLysTyrIlePheThrHisHisProIleTyrGlyGlyGlyLysValPro 670       680       690       700       710       720
ATGGTTTATGACCGTAATGAAACCACTCGCATTGAAGGTGGGGACGAACTTGTTCTTTCA
MetValTyrAspArgAsnGluThrThrArgIleGluGlyGlyAspGluLeuValLeuSer
```

Fig. 2-2

```
          730       740       750       760       770       780
AAAGATGTGCTTGCGGTTGGTATTTCTCAACGTACAGATGCTGCTTCTATTGAAAAATTG
LysAspValLeuAlaValGlyIleSerGlnArgThrAspAlaAlaSerIleGluLysLeu 790       800       810       820       830       840
TTGGTTAACATCTTTAAACAAAACCTTGGCTTCAAGAAAGTATTGGCCTTTGAATTTGCA
LeuValAsnIlePheLysGlnAsnLeuGlyPheLysLysValLeuAlaPheGluPheAla 850       860       870       880       890       900
AATAACCGTAAATTTATGCACTTAGACACTGTCTTTACCATGGTTGACTATGACAAATTT
AsnAsnArgLysPheMetHisLeuAspThrValPheThrMetValAspTyrAspLysPhe 910       920       930       940       950       960
ACCATTCACCCAGAAATTGAAGGAGACCTTCGTGTTTACTCTGTCACTTACGACAATGAA
ThrIleHisProGluIleGluGlyAspLeuArgValTyrSerValThrTyrAspAsnGlu 970       980       990      1000      1010      1020
GAACTTCATATCGTTGAAGAAAAAGGTGATTTAGCAGAACTTCTTGCTGCTAACCTTGGT
GluLeuHisIleValGluGluLysGlyAspLeuAlaGluLeuLeuAlaAlaAsnLeuGly 1030      1040      1050      1060      1070      1080
GTTGAAAAAGTTGACCTTATCCGTTGTGGTGGTGACAACTTAGTAGCAGCAGGTCGTGAA
ValGluLysValAspLeuIleArgCysGlyGlyAspAsnLeuValAlaAlaGlyArgGlu 1090      1100      1110      1120      1130      1140
CAATGGAACGATGGTTCTAACACCCTTACTATCGCACCAGGTGTGGTTGTGGTTTATAAC
GlnTrpAsnAspGlySerAsnThrLeuThrIleAlaProGlyValValValValTyrAsn 1150      1160      1170      1180      1190      1200
CGTAACACCATTACCAATGCTATTCTTGAATCTAAAGGCTTGAAATTGATCAAGATTCAC
ArgAsnThrIleThrAsnAlaIleLeuGluSerLysGlyLeuLysLeuIleLysIleHis 1210      1220      1230      1240      1250      1260
GGAAGTGAATTGGTTCGCGGTCGTGGTGGACCTCGTTGTATGTCAATGCCATTTGAACGT
GlySerGluLeuValArgGlyArgGlyGlyProArgCysMetSerMetProPheGluArg 1270      1280      1290      1300      1310      1320
GAAGATATTTAATAAGCTATGGTAAAGGTGGTTATAGGTCAGAAGCCTTTTTAAAGGGCA
GluAspIle 1330      1340      1350      1360      1370      1380
GCTAGTGTTTATCTTCGCTTCTGTGTCTTTGTCCTTCAATGAAATTTTGTCATGACAGAT 1390      1400      1410      1420      1430      1440
AAATTTGATGCCAATGACGAAACAAGAACGGTTTATGCAGTCGTTTATGACAATGACCAG 1450      1460      1470      1480      1490      1500
CCCGTTTCAACAGGACAATTTTTAGCTGAAACGAAAATAGAAGCACGATTGACACGCATT
```

Fig. 2-3

```
          1510      1520      1530      1540      1550      1560
     GTAACCTTAGCAGATTATTGTGGTTGCGGTTATGGTGCCAAAGTCACTGAAGCGCTAGAA 1570      1580      1590      1600      1610      1620
     ACTTATACCAGACGAGAAGGCTTTTACCAACTAACCATTCACAGTGAACTGACAGCACAA 1630      1640      1650      1660      1670      1680
     ACCTTTTATGAAAACCTAGGTTATCAGACCTATGGTTCCAAGTATTTAGAAGATGGTGAG 1690      1700      1710      1720      1730      1740
     TATTGTCAATCCCTTGTTAAAACCATTCTTAAATGGGAGAAGAATATGGACATAGCAATG 1750      1760      1770      1780      1790      1800
     CTAATTGCGATTGTTGGTGGTCTATTAGGCTGCTATCTCTATCTCACAAAAAATAATGAA 1810      1820      1830      1840      1850      1860
     CCCAAAGATTAAGTTAATACTCGAAGGAGACAATAGATGACACAAGTATTTCAAGGACGT 1870      1880      1890      1900      1910      1920
     AGCTTCCTAGCAGAAAAAGATTTTACACGCGCTGAATTAGAATACCTTATTGATTTTTCA 1930      1940      1950      1960      1970      1980
     GCTCATTTGAAAGATTTGAAAAAACGTGGTGTGCCTCATCACTACTTAGAAGGTAAAAAC 1990      2000      2010      2020      2030      2040
     ATTGCCCTCTTGTTTGAAAAAACATCAACTCGTACGCGTGCAGCTTTTACAACAGCAGCC 2050      2060      2070      2080      2090      2100
     ATTGACCTAGGTGCTCACCCAGAATACCTCGGTGCCAATGACATCCAACTTGGTAAAAAA 2110      2120      2130      2140      2150
     GAATCAACAGAAGACACTGCTAAAGTATTGGGTCGTATGTTTGATGGGATTGAATTC
```

ANTITUMOR PROTEIN GENE OF STREPTOCOCCUS PYOGENES SU, PLASMIDS CONTAINING THE GENE, TRANSFORMANT CELLS HARBORING THE PLASMIDS, AND PROCESS FOR PRODUCING THE ANTITUMOR PROTEIN

BACKGROUND OF THE INVENTION

The present invention relates to a gene of antitumor protein produced by *Streptococcus pyogenes*, a vector containing the gene and microorganisms or cells transformed with the vector, and a process for producing the antitumor protein.

*S.pyogenes* is a Gram-positive hemolytical coccus which is known as a pathogen of eryspelas, lochiopyra, and hematospesis. It is also known that strains of *S.pyogenes* have antitumor activities and the sterilized cells are now clinically used as an anticancer agent.

It is reported that the substance isolated from the cells of *S.pyogenes* Su by monitoring in vitro cell growth inhibition activity has been proved to have in vivo antitumor activity by experiments using animals [Yoshimura, Japanese Laid-Open Patent Publication (Kokai) No. 58-222026].

Yoshimura reports that this antitumor protein is a unique glycoprotein with a molecular weight of about 50,000 (analyzed by SDS-polyacrylamide gel electrophoresis), but its amino acid sequence has not yet been revealed, nor has a gene coding for the protein been isolated.

SUMMARY OF THE INVENTION

The present invention was completed by accomplishing the cloning of a gene coding for the antitumor protein of *S.pyogenes* (the protein will hereinafter be referred to as SAGP) and determining its total DNA sequence and amino acid sequence, producing vectors containing SAGP gene sequence and being capable of expressing SAGP in host cells, cultivating host cells transformed with the vectors and confirming the production of SAGP by the host cell. The invention makes it possible to produce SAGP safely on a large scale without cultivating pathogenic microorganisms.

The present invention provides an SAGP gene, DNA containing the gene, a recombinant plasmid containing SAGP gene and microorganisms or cells containing the plasmid, and a process for producing SAGP by cultivating the microorganisms or cells transformed with the plasmids. SAGP so obtained can be used as an antitumor agent.

BRIEF DESCRIPTION OF THE DRAWINGS

FIG. 1 shows a restriction map of plasmid pSP1.

FIG. 2 is the base seguence of an inserted DNA fragment of pSP1 and the amino acid sequence deduced from SAGP gene base sequence. The base number 40-1219 region is the region coding for SAGP. ATG, an initiation codon coding for Met exists upstream of the amino acid sequence coding for Thr of N terminal region of SAGP. The number of amino acids of SAGP is deduced to be 410.

DETAILED DESCRIPTION OF THE INVENTION

Figure 3:
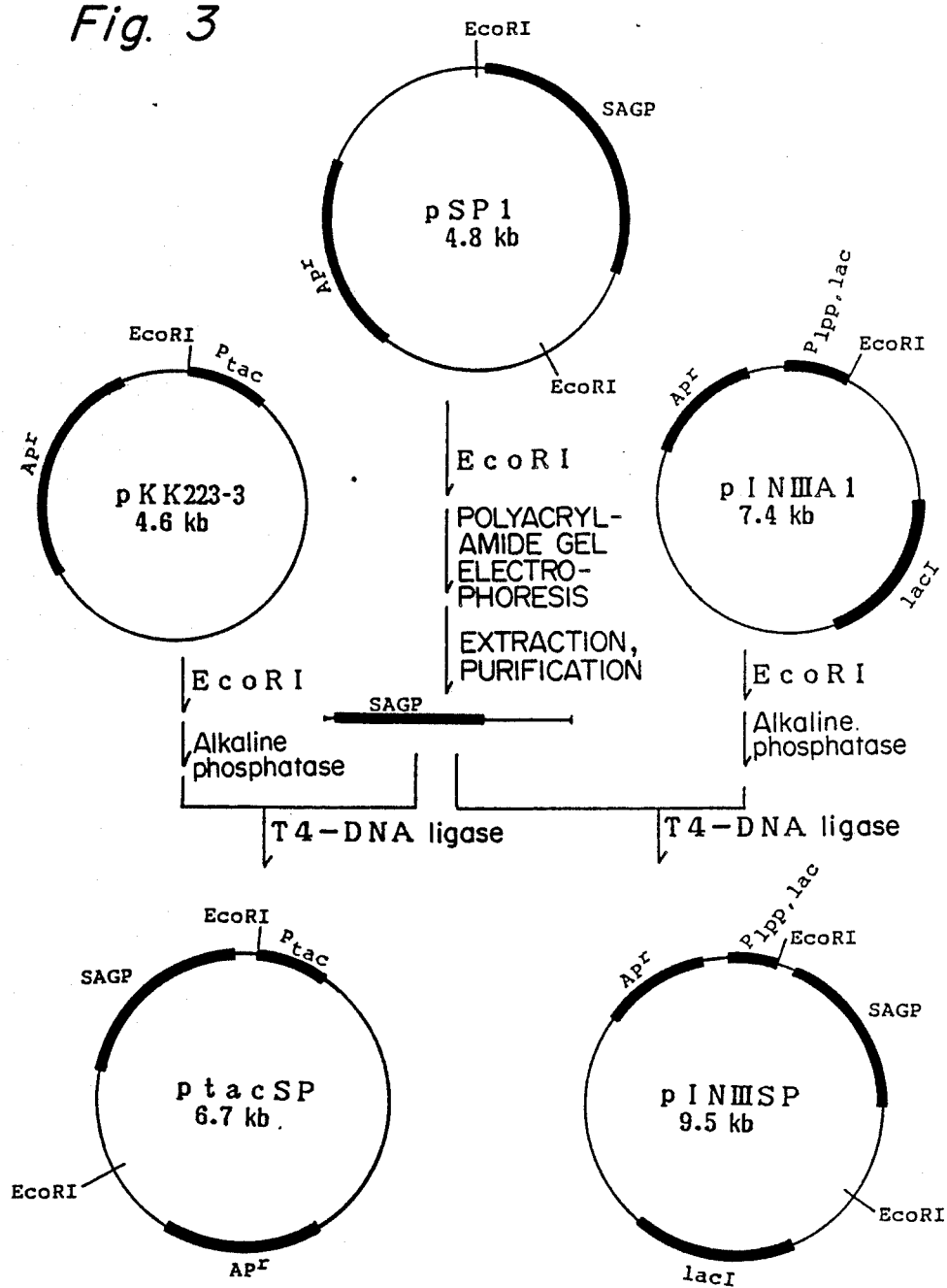
FIG. 3 shows a brief chart for illustrating construction of expression vectors having inserted thereinto a purified DNA fragment of SAGP gene prepared by digesting pSP1, plasmid containing SAGP gene, with EcoRI.

SAGP gene isolated from *S.pyogenes* by the present invention has the DNA sequence shown in FIG. 2 and, by using the information on the DNA sequence of FIG. 2, SAGP gene can now easily be isolated from *S.pyogenes* by procedures conventionally used in the field of the present invention.

SAGP gene isolated from *S.pyogenes* Su is, so to speak, natural DNA (base) sequence.

Today, the DNA synthesis technology makes it possible to synthesize DNA coding for a given protein, once the amino acid sequence of the protein is elucidated.

As is well know, most amino acids have more than one DNA base sequence or codon coding for them. Therefore, more than one DNA coding for a particular protein can be synthesized.

Accordingly, in synthesizing SAGP gene coding for the SAGP amino acid sequence in this invention, the DNA sequence is not limited to the natural SAGP gene DNA sequence, but contains all other DNA sequences coding for the SAGP amino acid sequence elucidated by the present inventors.

The present gene recombination technique can induce artificial mutation on a specific region of DNA sequence without making any substantial change or with an improvement of the basic characteristic of what is encoded by the DNA sequence.

As to SAGP gene of this invention, it is possible to prepare SAGP genes having the same or better characteristic as or than that of the natural SAGP gene by artificial insertion, deletion or substitution.

This invention encompasses such variant SAGP genes in addition to the natural gene.

Expression vectors which enable the production of SAGP in host cells can be prepared by inserting SAGP gene into suitable expression vectors using procedures commonly used in the field of the present invention.

Expression vectors used in this invention contain a SAGP gene sequence and a DNA sequence which controls the expression of SAGP gene in host cells upstream of the SAGP gene sequence, and are capable of replicating in the host cells.

More specifically, the expression vector essentially has a promotor sequence upstream of the SAGP gene and the origin of replication, i.e. DNA sequence controlling replication of the vector in a host cell.

As a promotor, known promotors such as lac promotor, trp promotor or lpp promotor can be used alone or in combination when *E.coli* is used as a host cell. These examples are not limitative, however.

In addition, the vector desirably contains a drug resistant gene to make it easy to select a host cell containing the vector.

For example, an ampicillin resistant gene and a tetracyclin resistant gene can be used as the drug resistant gene when *E.coli* is used as a host cell.

In the field of genetic engineering today, *E.coli* is most genetically analyzed and regarded as safest as host cells, and hence *E.coli* is most frequently used.

For the replication of SAGP gene and production of SAGP, it is desirable to use *E.coli*, as host microorganism, because *E.coli* can multiply rapidly and it is easy to control expression of SAGP gene in *E.coli*.

But it is possible to use some other kinds of bacteria, yeast, and so on, as a host cell together with adequate expression vectors which can replicate in microorganisms to be used.

Transformed *E.coli* is cultivated in a suitable medium and production of SAGP is confirmed by the Ouchterlony method or the Western blotting method.

SAGP may be isolated from the medium by methods conventionally used in the field of the invention.

The individual steps mentioned above will be described in detail.

1. Isolation of DNA fragment containing SAGP gene sequence:

SAGP gene may be isolated from *S.pyogenes* by a conventional method when the information on the DNA or amino acid sequences of SAGP given by the invention is used. More specifically, it can be isolated for example, through the following procedures:

(1) Synthesis of probes, short length DNA that is complementary to SAGP gene:

Short length DNA's each of which has the base sequence complementary to the DNA sequence of SAGP gene described in FIG. 2 are synthesized.

It is possible to obtain adequate probes by determining the amino acid sequence of purified SAGP gene, deducing a DNA sequence from the amino acid sequence and synthesizing short length DNAs which have the deduced DNA sequence.

(2) Extraction of *S.pyogenes* chromosomal DNA and digestion with restriction enzyme and fractionation.

After cultivation of *S.pyogenes*, the cells are lysed with an enzyme and/or a detergent, then the chromosomal DNA is extracted and purified from the lysed cells by a known method [J. Maromor J. Mol. Biol., 3, 280 (1961)]. The extracted chromosomal DNA is digested with a restriction enzyme.

The digested chromosomal DNA is subjected to agarose gel electrophoresis, and then fractionated according to the length of DNA fragments.

The DNA fragments are transferred and immobilized on a nitrocellulose filter by the Southern's method [E. M. Southern, *J. Mol. Biol.*, 98, 503 (1975)]. By Southern hybridization with the RI-labeled DNA probes, the length of DNA fragments containing SAGP gene was determined.

(3) Insertion of the DNA into a vector and transformation of host *E.coli* with the resulting recombinant vector:

DNA fragments of such a size that contains SAGP gene are isolated from the digested chromosomal DNA fragments fractionated by agarose gel electrophoresis and then ligated with vector DNA previously digested with the same restriction enzyme by DNA ligase. The ligation mixture is introduced into *E.coli* to give transformed cells.

(4) Selection of transformant carrying SAGP gene:

The transformants obtained in (3) are grown on a nitrocellulose filter and lysed, and then the DNA fragment from lysed cells is immobilized on the filter. By hybridization of the immobilized DNA fragment described above with RI-labeled probe, the transformed cells containing SAGP gene is identified.

(5) Isolation of Plasmid DNA:

The transformants determined to contain SAGP gene as in (4) are cultivated, and then plasmid DNA is isolated from them by a known method [T. Maniatis, E. F. Fritsch, J. Sambrook, Molecular Cloning, p.86, Cold Spring Harbor Laboratory (1982)].

(6) Preparation of a restriction enzyme map of plasmid DNA:

The plasmid DNA isolated in (5) is digested with restriction enzymes, the length of each fragment is determined by electrophoresis and a restriction enzyme map of the plasmid DNA is prepared.

(7) Determination of DNA sequence of SAGP gene:

Based upon the restriction enzyme map prepared in (6), SAGP gene DNA is digested into shorter length fragments with restriction enzymes and each fragment is cloned. Then, its base sequence is determined by the Sanger method, [G. F. Hong, *Biosci.Report*, 2, 907 (1982)].

In addition, the base sequences of the DNA fragments are also determined by the Maxam-Gilbert method [A. Maxam and W. Gilbert, Method in Enzymology, 65,499 (1980)].

(8) Isolation of DNA fragment containing SAGP gene sequence from the plasmid vector carrying the gene:

Plasmid vector containing SAGP gene sequence is digested with a restriction enzyme.

The DNA fragments of digested vector are fractionated by polyacrylamide gel electrophoresis, and a 2100 base pair DNA fragment containing SAGP gene is extracted and purified from the gel.

2. Construction of expression vector:

SAGP gene is inserted into an expression vector.

For example, commercially available plasmid pKK 233-3 or pIN III is digested at a site downstream of the promotor with restriction enzyme EcoRI, and mixed with DNA fragment containing SAGP gene described above and ligated with T4-DNA ligase.

3. Transformation of host *E.coli*

The expression vector ligated with DNA containing SAGP gene is introduced into *E.coli* by a conventional transformation method.

Plasmid DNA is prepared from the transformants obtianed above and the transformant containing expression vector is selected by analyzing its restriction enzyme digestion pattern.

4. Cultivation of transformed *E.coli* and induction of expression of SAGP gene:

*E.coli* transformed by the expression vector described in 3 is inoculated and incubated in a liquid medium at 37° C.

Growth of bacteria is observed by measuring the optical density of the culture medium and at the proper step of growth, expression of SAGP gene is induced by adding Isopropyl-$\beta$-D-thiogalactoside (IPTG), for example. After that, the transformants are further cultivated.

5. Harvest of cells and isolation of SAGP

The liquid culture described in 4 is centrifuged to harvest the cells.

The harvested *E.coli* cells are lysed with lysozyme, or a detergent, or by sonification, for example and SAGP can be isolated from the mixture by a conventional method.

SAGP is purified from all the lysate through analogous methods adopted for purification of SAGP from cultured cells of *S.pyogenes* Su; they are ammonium sulfate precipitation, Octyl-Sepharose CL-4B column chromatography, DE-52 ion-exchange chromatography and TSK gel G3000SW gel filtration.

Production of SAGP is confirmed by analyzing the lysed mixture by the Ouchterlony method or the western blotting method.

EXAMPLE 1

1. Isolation of SAGP gene (1) Determination of amino acid sequence of N-terminus of SAGP SAGP was purified by a known method (Yoshimura, Japanese Patent Publication (Kokai) No. 58-222026) from S.pyogenes Su. (ATCC 21060) and using purified SAGP 100 μg, the amino acid sequence of N terminus was analyzed by gas-phase protein sequencer (Applied Biosystems Model 470A). As a result, the amino acid sequence of N-terminus of SAGP was determined as follows:

Pro (or Thr)-Ala-Glu-Thr-Pro-Ile-Unk-Val -Tyr-Unk-Unk-Ile-Gly-Lys-Leu-Lys-Lys-Val-Leu -Leu-His-Unk-Pro-Gly-Lys

In the formula, Unk means "unknown".

(2) Synthesis of Probe

Based upon the amino acid sequence determined above, 2 kinds of mixed probe P-37 and P-38, short length DNA fragments coding for a part of the amino acid sequence, were synthesized.

The P-37 corresponds to the amino acid sequence Pro-Ala-Glu-Thr-Pro-Ile, and contains DNAs of the following sequences:

CC(T,A)GC(T,A)CAAAC(A,T)CC(T,A)AT-(A,T)T.

The P-38 corresponds to the amino acid sequence Ile-Gly-Lys-Leu-Lys-Lys-Val, and contains DNAs of the following sequences:

AT(T,A)GG(T,C)AAATT(A,G)AAAAAAGT.

The P-37 is a mixture of 32 kinds of DNA sequences and P-38 is a mixture of 8 kinds of DNA sequences, as mentioned above.

They were synthesized by automatic DNA synthesizer (Applied Biosystems Model 380A) to yield 146 μg of the P-37 and 244 μg of the P-38.

These probe DNA were $^{32}$P-labeled as follows just before the hybridization.

Synthetic probe 5pM was incubated with T4-polynucleotide kinase and $(\gamma^{32}p)$-ATP30 Ci at 37° C. for 30 minutes.

After the reaction product was adsorbed on a small amount of DE-52, and nonreacted $(\gamma^{32}p)$-ATP was washed away with 0.1M-NaCl solution, $^{32}$p-labeled probe was extracted from the DE-52 with 1M-NaCl solution.

(3) Extraction and digestion with restriction enzyme of chromosomal DNA of S.pyogenes Su S.pyogenes Su (ATCC 21060) was cultivated in L culture medium 300 ml at 37° C. for 15 hours, and then cells were harvested by centrifugation.

The cells were suspended in 0.15M NaCl - 0.1M EDTA solution, and lysed with lysozyme, pronase and sodium dodecylsulfate (SDS).

Chromosomal DNA was extracted from the lysate, and purified by a known method [J. Marmur, *J. Mol. Biol.*, 3, 208 (1961)]

The chromosomal DNA 5 μg was incubated with restriction enzyme EcoRI at 37° C. for 1 hour and the digested DNA was subjected to 1% agarose gel electrophoresis.

This agarose gel was soaked in 0.2M NaOH-0.5M NaCl solution, so that DNA was denatured, and washed with tria-acetate-EDTA buffer for 10 minutes 3 times.

Then DNA on agarose gel was electrophoretically transferred to Zeta-Probe filter. (Electrophoresis was done at 30V overnight). The filter was heated at 80° C. for 3 hours after air-drying at room temperature for 30 minutes.

Two Zeta-Probe filters on which DNA was immobilized by the above method were prehybridized with 4×SSC [Blin et al., *Nucleic Acid Research*, 3, 2303 (1976)], 50×Denhart [Wahl et al., *Proc.Natl.Acad.Scie.*, 76, 3683 (1979)], 1% SDS and sonicated salmon sperm DNA solution 10 μg/ml at 60° C for 3 hours.

Then, the filters described above were hybridized with the same solution containing 100,000 cpm labeled P-37 probe or P-38 probe at 40° C. for 18 hours.

The filters were air-dried after 4 times washing with 4×SSC at 40° C. 15–30 minutes, and then exposed to X-ray films for 48 hours.

As a result, both hybridization with P-37 probe and with P-38 probe revealed that there exists a band hybridized on the position of about 2 kbp DNA fragment.

(4) Insertion of chromosomal DNA fragment into vector and transformation of E.coli Chromosomal DNA 50 μg was digested by incubating it with restriction enzyme EcoRI at 37° C. for 1 hour and then applied to 1% agarose gel electrophoresis. The regions of the gel containing about 1.8–2.2 kbp fragment was cut out, from which DNA fragment was extracted.

The chromosomal DNA mentioned above was mixed with plasmid vector pUC19 (Takara Shuzo) digested with EcoRI and reacted with T4-DNA ligase at 17° C. overnight. E.coli JM103 was transformed with the reaction mixture [M. Mandel and A. Higa, *J. Mol. Biol.*, 53, 159 (1970)], inoculated on L-agar medium containing 5-bromo-4-chloro-3-indolyl-β-D-galactoside (X-Gel), isopropyl-β-D-thiogalactoside (IPTG) and ampicillin and then cultivated at 37° C. overnight, from which sixty-four white colonies were picked up.

(5) Selection of transformant carrying SAGP gene

Each of the sixty-four transformed E.coli JM103 obtained above was inoculated in nitrocellulose filter on L-agar medium and cultivated at 37° C. for 6 hours.

The filter was transferred to L-agar medium containing ampicillin, chloramphenicol and cultivated at 37° C. overnight.

After cultivation, the filter was treated with 10% SDS for 5 minutes, with NaOH-1.5M NaCl for 3 minutes, and with 1M tris - HCl butter for 5 minutes so that bacteria on the filter were lysed. The DNA of them was immobilized on the filter by heating it at 80° C. for 3 hours.

Hybridization with the labeled P-38 probe described above and exposure to X-ray film revealed that two colonies among sixty-four colonies were hybridized with the probe.

(6) Isolation of Plasmid DNA

Two colonies revealed to have SAGP gene were cultivated and plasmid DNA was obtained by a known method [T. Maniatis, E. F. Fritsch, J. Sambrook, Molecular Cloning, p.86, Cold Spring Harbor Laboratory (1982)].

The plasmid DNA obtained from the two positive clones were analyzed with several restriction enzymes. Consequently they represented the same restriction pattern, and were found to be identical to each other. They were named pSP1.

(7) Preparation of pSP1 restriction map

Plasmid pSP1 obtained above was digested with restriction enzymes, EcoRI, HindIII, PstI, ClaI, NcoI, AvaII, HpaI, HincII, AhaIII, BanI, HaeII, MluI independently or in combination, and the digested DNA fragments were applied to agarose gel or acrylamide gel electrophoresis to determine the length of fragments to prepare the restriction map of pSP1.

Consequently, it was revealed that pSP1 was a plasmid wherein about 2 kbp foreign DNA fragment was inserted into the EcoRI site of pUC19.

(8) Determination of SAGP gene DNA sequence

Based upon the restriction map described above, inserted DNA fragments of pSP1 were further digested with restriction enzymes and cloned into pUC19, and using them, DNA sequencing was carried out by the dideoxy method [G. F. Hong, Biosci.Report, 12,907 (1982)]. Sequencing kit manufactured by Takara Shuzo, and M-4 or RV as a primer (Takara Shuzo) was used. The DNA sequence of each fragment was determined to elucidate the entire 2157bp sequence containing SAGP gene.

(9) Isolation of DNA fragment containing SAGP gene from the plasmid vector

Plasmid pSP1 containing SAGP gene sequence obtained above 12.5 μg was digested with restriction enzyme EcoRI (Takara Shuzo) 50 units at 37° C. for 2 hours.

This digested mixture was fractionated with 5% polyacrylamide gel electrophoresis and the region of the gel containing DNA fragment of 21000 bp was cut out.

DNA was extracted from the cut out gel with Tris-EDTA buffer.

The extract was purified by washing with phenol and precipitation with ethanol to give 21000 bp DNA fragment containing SAGP gene.

2. Construction of expression vector

Two micrograms of pKK 223-3 (Pharmacia-PL), a plasmid DNA for construction of expression vector containing trp and lac promotors (tac promotor) and ampicillin resistant gene was digested with restriction enzyme EcoRI 6 unit at 37° C. overnight which was then reacted with alkaline phosphatase at 37° C. for 30 minutes to remove 5'terminal phosphate residue.

DNA was recovered from the mixture by washing with phenol and precipitation with ethanol.

pIN III A1 plasmid DNA containing lpp and lac promotor and ampicillin resistant gene [Inouye EMBO Journal, 1, 771 (1982)] was digested with EcoRI and 5'terminal phosphate was removed with alkaline phosphatase by the same method as above. The DNA fragment containing SAGP prepared in 1, 9 above was mixed with the vector DNAs described above, and the mixtures were reacted with T4-DNA ligase (Takara Shuzo) at 4° C. overnight to ligate them and produce expression vectors PIN III SP and ptac SP, as illustrated in FIG. 3.

3. Transformation of host E.coli

E.coli JM 103 was transformed by a known method [T. Maniatis, Molecular Cloning, p.250, Cold Spring Harbor Laboratory (1982)] with the expression vector described above.

20-30 clones for each transformant obtained above were cultured and their plasmid DNA was isolated by a known method (T. Maniatis, Molecular Cloning, p.86, Cold Spring Harbor Laboratory) and digested with various kinds of restriction enzymes. The digestion patterns were analyzed by agarose gel electrophoresis, so that clones of transformant E.coli JM103 (pIN III SP) (ATCC 67271), carrying pIN III SP and E.coli JM103 (ptac SP) (ATCC 67272) carrying ptac SP were selected.

4. Cultivation of transformed E.coli and induction of the expression of SAGP gene Each of the transformed E.coli cells carrying expression vector described above was inoculated in LB medium (T. Maniatis, Molecular Cloning, p.440, Cold Spring Harbor Laboratory) 100 ml, and incubated at 37° C.

Growth of the culture was observed by measuring its optical density at 550 nm. When $OD_{550}$ reached 0.2, IPTG(Isopropyl-β-D-thiogalactoside) 0.1 mM (final concentration) was added to the medium and expression of SAGP was induced. The cultivation was continued.

After the induction, a small amount of the medium was periodically taken out to examine production of SAGP.

At the same time, E.coli harboring pKK 233-3 or pIN III A1 was cultivated and IPTG was added. The medium was examined in the same way as controls.

5. Confirmation of the production of SAGP

Cells in the sampled culture medium described above were harvested by centrifugation and the harvested cells were lysed by reacting with lysozyme 2 mg/ml at 0° C. for 30 minutes, and adding 1% Triton-X100 (Wako Pure Chemicals Co., Ltd.).

When the lysate was reacted with anti-SAGP rabbit antiserum by Ouchterlony method [O. Ouchterlony, Prog. Allergy, 6, 30 (1962)] at 37° C. overnight, an obvious sedimentation line was represented by the antigen-antibody reaction if it was the lysed mixture of the cells containing pIN III SP or ptacSP, or SAGP isolated from S.pyogenes. In the case of mixtures containing pIN III A1 or pKK 233-3, as control experiment, no sedimentation line was observed.

The lysed mixture was fractionated by 12.5% SDS-polyacrylamide gel electrophoresis, and the protein was transferred to a nitrocellulose filter by Western blotting method [W. N. Burnette, Anal. Biochem., 112, 195 (1981)] and immobilized.

The filter was soaked in a buffer solution containing anti-SAGP rabbit antiserum at 37° C. for 30 minutes, and also at 40° C. overnight. Unreacted anti-SAGP antibody was washed away with the buffer, and the filter was soaked in a buffer solution containing alkaline phosphatase-anti-rabbit IgG antibody at 37° C. for 2 hours, whereby anti-SAGP antibody on the filter was reacted with it.

When the filter was washed and soaked in the buffer containing BCIP (5-Bromo-4-chloro-3-indolylphosphate) for coloration, a band formed by the antigen-antibody reaction was observed in the same molecular weight (Ca. 47,000 daltons) region as SAGP isolated from S.pyogenes in the cases of the transformant E.coli containing ptac SP or pIN III SP.

Another E.coli containing pKK 233-3 or pIN III A1, used as control experiment, did not represent such band.

Accordingly, production of SAGP by E.coli containing expression vectors discribed above was confirmed.

EXAMPLE 2

Purification and N-terminal amino acid sequence of SAGP produced in E.coli JM103(ptacSP)

In order to confirm the amino acid sequence of the expressed protein in E.coli, the expressed protein was purified and the N-terminal amino acid sequence was determined as follows.

(1) Assay Method

At each step of the purification process, the fractions containing SAGP were determined by an enzyme linked immunosorbent assay method.

The samples and the standard SAGP were diluted by phosphate buffered saline (PBS), containing NaCl 8g, KCL 0 2g, NaHPO$_4$.12H$_2$O 2.9g and KH$_2$PO$_4$ 0.2g per liter, and 100 μl of diluted solutions was put into each well of a 96-well flexible assay plate (Falcon®3912) which had been washed by distilled water. After the plate was maintained at 37° C. for 2 hours, solutions in the wells were removed and 200 μl blocking solution (2% bovine serum albumin and 0.05% Tween®20 in PBS) was poured into the each well and placed at 37° C. for 2 hours. The blocking solution was removed and then the assay plate was washed with PBST (0.05% Tween®20 in PBS). Then 100 μl of the anti-SAGP rabit anti-serum which was diluted to 10000-fold by PBST containing 1% BSA was put into each well and the plate was maintained at 37° C. for 2 hours. After the anti-serum solution was removed, the assay plate was washed with PBST. Then 100 μl of alkaline phosphatase linked anti-rabit-IGg anti-serum (Miles Scientific) which was diluted to 3000-fold with PBS was put into each well and the assay plate was maintained at 37° C. for 2 hours. After the enzyme linked anti-serum solution was removed, the assay plate was washed with PBST. Then 100 μl of a substrate solution which contained 0.3% disodium p-nitrophenylphosphate in 10% diethanolamine buffer (pH 9.1) was put into each well and the assay plate was maintained at 37° C. for 15 minutes. To stop the enzyme reaction, 20 μl each of 1N NaOH was added. SAGP contained in sample solutions was identified and quantified by measuring the absorbance of 450 nm light of the reaction mixtures.

(2) Cultivation of *E.coli* JM103(ptacSP)

The cells of *E.coli* JM103(ptacSP) maintained on a LB-agar medium containing 50 μg/ml ampicillin were inoculated and cultivated in 5 ml LB medium containing 100 μg/ml ampicillin in test tubes for 14 hours at 37° C. Five mili-liters of the pre-culture broth was inoculated in 12 flasks of 2-liter volume each containing 500 ml LB-ampicillin (100 μg/ml) medium. Then the *E.coli* cells were cultivated at 37° C. for 24 hours in a rotary shaker (New Brunswick Scientific Inc. model G-25) at 280 rpm.

After the cultivation, the cells were harvested using a TOMY RS-20BH centrifuge equipped with a BH-9 rotor (10000 rpm, 10 min).

The separated cells were resuspended in 200 ml PBS and lysed by using a BRANSON SONIFIER. The ruptured cell suspension was centrifuged (TOMY BH-9 rotor 10000 rpm, 10 min) and the pellet was removed.

(3) Ammonium sulfate precipitations

The supernatant of the cell lysate was brought to 20% saturation with respect to ammonium sulfate and was stirred for 2 hours at 4° C. followed by standing for 2 hours. The solution was centrifuged (Sorvall GSA rotor 10000 rpm, 15 min) and the pellet was removed. Then the supernatant was brought to 70% saturation with respect to ammonium sulfate and stirred for 2 hours at 4° C. followed by standing overnight. The solution was centrifuged (Sorvall GSA rotor 10000 rpm, 15 min) and the pellet was recovered.

(4) Octyl-Sepharose CL-4B column chromatography

The ammonium sulfate precipitate described above was dissolved in 6 ml of 10 mM potassium phosphate (pH 7.0) and applied to an Octyl-Sepharose CL-4B (Pharmacia) column (25φ×600 mm), which had previously been equilibrated with 10 mM potassium phosphate (pH 7.0). The chromatography was performed by 800 ml of 10 mM potassium phosphate (pH 7.0) with ethylene glycol gradient (from 0 to 50%); flow rate 1 ml/min, 8 ml/fraction. The fractions from No. 22 to No. 38 were collected and dialysed against distilled water then lyophilized.

(5) DE-52 ion-exchange chromatography

The SAGP fraction mentioned above was then dissolved in 5 ml of 10 mM potassium phosphate (pH 7.0) and applied to an DE-52 (Whatman) column (15φ×600 mm), which had been previously equilibrated with 10 mM potassium phosphate (pH 7.0). Chromatography was performed by 800 ml of potassium phosphate (pH 7.0) with the salt concentration gradient (from 10 to 500 mM); flow rate 0.7 ml/min, 8 ml/fraction. The fractions from No. 48 to No. 58 were collected, dialysed against distilled water, and then lyophilized.

(6) DEAE-Sephadex ion-exchange chromatography

The SAGP fraction mentioned above dissolved in 5 ml of 10 mM sodium phosphate (pH 7.0) and applied to an DEAE-Sephadex A-25 (Pharmacia) column (15φ×500 mm), which had been previously equilibrated with 10 mM sodium phosphate (pH 7.0). Chromatography was performed by 300 ml of 10 mM sodium phosphate with NaCl gradient (from 0 to 500 mM); flow rate 0.35 ml/min, 3 ml/fraction. The fractions from No. 56 to No. 66 were collected, dialysed against distilled water, and then lyophilized.

(7) TSK G-3000SW gel filtration

The SAGP fraction mentioned above was dissolved in 2 ml of PBS and 200 μl of the solution was applied to a TSK G-3000SW (Toyo Soda) gel filtration HPLC column (7.5×600 mm). Chromatography was performed by using PBS as an eluant; flow rate 0.3 ml/min. The eluate whose retention time was from 53.5 min to 56.8 min was recovered. This gel filtration was repeated once.

The recovered solution was desalted by using a Sephadex PD-10 (Pharmacia) column, and then lyophilized.

(8) SDS-polyacrylamide gel electrophoresis

The recovered eluates mentioned above was then applied to a 12.5% SDS-polyacrylamide gel electrophoresis and a gel piece which contained a protein whose mobility corresponded to a molecular weight 4.7 kg was cut out.

The protein in the gel piece was electrophoretically eluted by a known method [M. W. Hunkapiller et al, Methods in Enzymology, 91, 227 (1983)].

(9) N-terminal amino acid sequencing

The protein recovered from the SDS-polyacrylamide gel mentioned above was applied to a Protein Sequencer model 470A (Applied Biosystems).

The deduced N-terminal amino acid sequence was as follows.

Thr-Ala-Gln-Unk-Pro-Ile-Unk-Val-Tyr

The amino acid sequence was in agreement with the N-terminal portion of SAGP produced by *S.pyogenes* Su without the 4th and the 7th amino acids; they are threonine and histidine in the native SAGP and both of them are hardly detectable by the adopted sequencing method. Since methionine was also detected as the N-terminus together with threonine by the amino acid sequencing, it was not denied that the SAGP produced by *E.coli* contained a protein whose N-terminal methionine was not processed.

Thus it was confirmed that the cloned gene was correctly translated to the amino acid sequence of SAGP.

What is claimed is:

1. Isolated DNA coding for antitumor protein produced by *Streptococcus pyogenes* which is characterized in that the DNA sequence coding for the antitumor protein is specified by the amino acid sequence described in FIG. 2.

2. Isolated DNA according to claim 1, which is characterized by coding for an antitumor protein having the base sequence described in FIG. 2.

3. Isolated DNA containing a DNA sequence coding for an antitumor protein produced by *Streptococcus pyogenes* which is characterized in that the antitumor protein is specified by the amino acid sequence described in FIG. 2.

4. Isolated DNA according to claim 3, which is characterized in that the DNA coding for the antitumor protein is of the base sequence described in FIG. 2.

5. DNA according to claim 3, which is self-replicating.

6. Isolated DNA according to claim 5, which is specified as plasmid pSP1.

7. Expression vector which harbors DNA coding for an antitumor protein and which expresses the antitumor protein in host cells, said antitumor protein having the amino acid sequence described in FIG. 2.

8. Expression vector according to claim 7, which is characterized in that the DNA has the DNA sequence described in FIG. 2.

9. Expression vector according to claim 7, which is specified as ptac SP.

10. Expression vector according to claim 7, which is specified an pIN III SP.

11. Expression vector according to claim 7, which is characterized in that the host cell is *E. coli*.

12. A microorganism containing DNA coding for an antitumor protein produced by *Streptococcus pyogenes*, said microorganism being specified as *E. coli* JM 103 (pSP1) (ATCC 67270).

* * * * *